United States Patent [19]

Heelies

[11] Patent Number: 4,883,760

[45] Date of Patent: Nov. 28, 1989

[54] DEVICE FOR PERFORMING ENZYME IMMUNOASSAYS

[75] Inventor: Donald R. Heelies, Mississauga, Canada

[73] Assignee: Adi Diagnostics Inc., Rexdale, Canada

[21] Appl. No.: 209,332

[22] Filed: Jun. 20, 1988

[51] Int. Cl.$^4$ ............................................. C12M 1/24
[52] U.S. Cl. .................................. 435/296; 435/287; 435/810; 426/535; 422/51
[58] Field of Search ............... 435/296, 287, 288, 291; 422/56, 58, 7; 436/518, 548; 426/808, 818, 535

[56] References Cited

U.S. PATENT DOCUMENTS

| | | |
|---|---|---|
| 4,053,284 | 10/1977 | Posch . |
| 4,087,248 | 5/1978 | Miles . |
| 4,116,638 | 9/1978 | Kenoff . |
| 4,276,048 | 6/1981 | Leaback . |
| 4,623,461 | 11/1986 | Hossom et al. . |
| 4,632,901 | 12/1986 | Valkirs et al. . |
| 4,665,034 | 5/1987 | Chandler . |
| 4,699,884 | 10/1987 | Noss et al. ........................ 435/287 |
| 4,791,060 | 12/1988 | Chandler ........................... 435/296 |

FOREIGN PATENT DOCUMENTS

| | | |
|---|---|---|
| 1191786 | 8/1985 | Canada . |
| 2530957 | 2/1976 | Fed. Rep. of Germany . |
| 2389134 | 11/1978 | France . |
| 2005831B | 10/1982 | United Kingdom . |

OTHER PUBLICATIONS

Science, vol. 158, (1967), pp. 1570 to 1572—Catt and Tregear.
Acta Endocrinol. (Copenhagen) Supplement 202, (1976), pp. 33 to 35—Friedel.
Autorenreferate der Jahrestagung, (1977), pp. 185 to 186—Schweer, Friedel and Trautchold.
European Journal of Nuclear Medicine, vol. 5, (1980), pp. 423 to 425—Zick et al.
Medical Laboratory Sciences, vol. 40, (1983), pp. 287 to 289—Chandler, Healey and Hurrell.

Primary Examiner—Larry Jones
Attorney, Agent, or Firm—Ridout & Maybee

[57] ABSTRACT

The device has a transparent capillary assay tube attached at its upper end to a lateral portion of the support structure of the device. The lower free end of the assay tube is engageable with an absorbent material upon manual downward deflection of the support structure. The assay tube is filled through a funnel shaped aperture in the lateral portion of the device, and the tube is drained by engaging the lower free end of the tube with the absorbent material. By attaching appropriate antibody, antigen or hapten to the inner surface of the tube, immunoassays may be performed in the tube.

14 Claims, 1 Drawing Sheet

DEVICE FOR PERFORMING ENZYME IMMUNOASSAYS

This invention is a device for performing enzyme immunoassays which provides a simple and reliable means for carrying out basic diagnostic tests quickly and accurately at home or in a doctor's office.

With the relatively recent advent of immunoassay techniques including the advances involving the use of monoclonal antibodies, it has become possible to carry out a wide variety of diagnostic medical tests as well as other tests quickly and accurately using very small test samples. For example, a woman can test for pregnancy using a few drops of blood or urine and a testing kit which utilizes presently available immunoassay techniques, the testing procedure being simply performed with a result obtainable in about five minutes.

In order to bring immunoassays out of the laboratory and make this technology generally available to untrained users, it has become necessary to develop testing devices which may be reliably used by the non-technician to perform desired tests at the user's convenience. A principal concern in creating such testing devices heretofore has been to provide a user friendly device having a low probability of misuse leading to a false result. A number of approaches to the development of suitable devices for performing immunoassays can be seen from a review of the prior art, including art of the assignee of the present application. Thus, U.S. Pat. Nos. 4,585,623; 4,665,034; 4,690,801; and 4,729,875 provide a number of approaches to the development of a simple yet reliable testing device.

Regardless of the particular merits of any of the known prior art devices, an underlying problem with all prior devices is the degree of mechanical or structural sophistication they require, which in turn demands a high level of quality control in their manufacture. Accordingly, it may not be possible presently to mass produce one of these fairly intricate yet user friendly devices at a cost which would be competitive with present laboratory testing procedures.

The invention provides a device for performing enzyme immunoassays which is simple in design so that it can be manufactured at low cost with a reasonable level of quality control. The invention probably requires the user to follow assay procedures carefully in order to obtain a correct result, but with the advent of presently available monoclonal assay techniques, these procedures are thought to be sufficiently simplified so that most users will have no difficulty correctly performing the assay on the first attempt to do so.

Accordingly, the present invention provides a device for performing immunoassays, comprising a support structure for a transparent capillary tube having an internal surface to which is attached an antibody, antigen or hapten. The tube has an upper end which is attached to a lateral portion of the support structure so that the tube is suspended in an upright position having a lower end of the tube being free. The support structure defines an aperture which is in flow communication with the upper end of the tube, and the support structure has an upright portion attached to the lateral portion. The upright portion is sufficiently resiliently flexible to allow downward deflection of the lateral portion, and hence, the tube upon application of moderate manual pressure. Absorbent material is positioned beneath the capillary tube and is spaced from the lower free end thereof. The lower end of the tube is engageable with the absorbent material upon downward deflection of the support structure so that liquid contained in the capillary tube may be drawn into the absorbent material.

Figure 1:
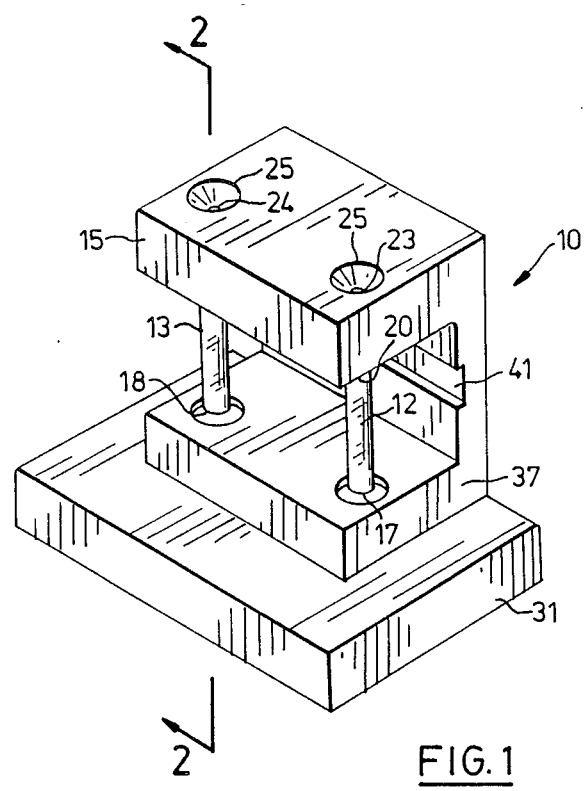
FIG. 1 is a perspective of the device of the invention.

As shown in the drawings, a preferred embodiment of the invention comprises a support structure 10 for at least one transparent capillary tube 12 having an internal surface to which is attached, such as by covalent bonding, an antibody, antigen or hapten chosen for binding with a target molecule in accordance with the assay to be conducted. The basic device of the invention preferably has two capillary tubes, the assay tube 12 and a reference tube 13 having no antibody, antigen or hapten attached to its internal surface. The reference tube 13 is used for comparison purposes with the assay tube 12 to assist the user in judging the assay result, usually indicated by the formation or lack of formation of a particular colour. The reference tube 13 should always indicate a negative result. A suitable capillary tube for utilization in the present device is a glass or clear plastic tube having a bore diameter of about 1 mm and a length of about 25 mm.

The tubes 12 and 13 are attached to the lateral portion 15 of the support structure 10 so that they extend downwardly from the lateral portion 15 with their lower ends 17 and 18 being free. The upper ends 20 and 21 of the tubes 12 and 13 are attached to the lateral portion 15 in flow communication with apertures 23 and 24 defined in the lateral portion 15. Preferably, the apertures 23 and 24 have at least upper conically shaped portions 25 which provide funnelled feed wells for introducing liquids into the tubes 12 and 13

Figure 3:
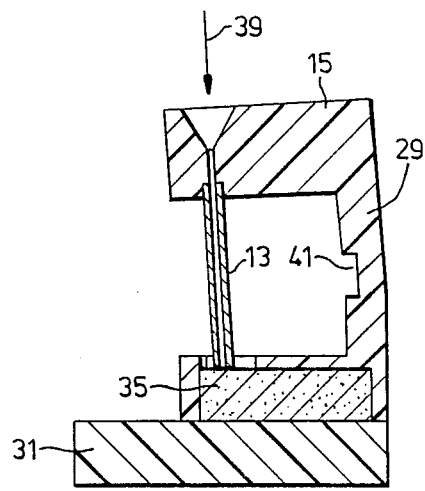
FIG. 3 is the same cross sectional view as FIG. 2 with the upright portion being flexed thereby allowing downward deflection of the lateral portion and the tube.

The support structure has an upright portion 29 which extends downwardly from the lateral portion 15 preferably to a base 31. Positioned atop the base 31 and beneath the lower ends 17 and 18 of the tubes 12 and 13 is a body of absorbent material 35 preferably surrounded by a containment structure 37 which encloses the absorbent material 35 except in the area beneath the tubes 12 and 13 thereby allowing the tube ends 17 and 18 to be engageable with the absorbent material 35 in the manner described below. The upright portion 29 is sufficiently resiliently flexible to allow downward deflection of the lateral portion 15 upon the application of moderate manual pressure (arrow 39, FIG. 3). The upright portion 29 may be made sufficiently resiliently flexible by the choice of material and structure of the portion 29. Preferably, the upright portion 29 is made of a plastic, and advantageously may be molded as a unit with other parts of the device. The upright portion 29 may be provided with one or more transverse grooves 41 for the purpose of inducing the desired degree of flexibility into the structure of the upright portion 29.

Figure 2:
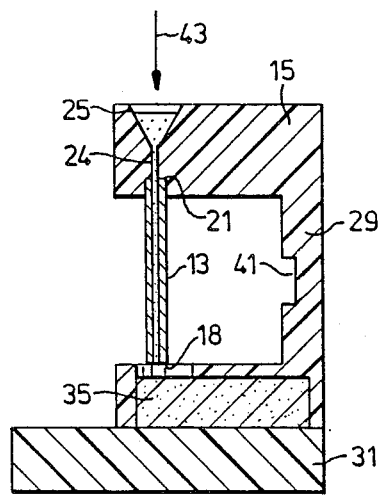
FIG. 2 is a cross sectional view as indicated from FIG. 1 showing the upright portion of the device in the normal position.

The device may be used to perform a wide variety of immunoassays. As an example, pregnancy may be tested by assaying for the presence of human chorionic gonadotropin (HCG) in the blood or urine. An antibody specific to HCG (anti-HCG) may be attached to the internal surface of the assay tube 12 and a blood or urine specimen may be introduced into the tube 12 through the aperture 23 by placing two drops of the specimen in the conical well 25 (arrow 43, FIG. 2). The surface tension of the liquid will allow the test specimen to remain in the assay tube 12 until it is drained from the tube 12 by deflecting the lateral portion 15, and consequently, the tube 12 downwardly so that the lower end 17 of the tube 12 engages the absorbent material 35. As mentioned this downward deflection is accomplished manually, finger pressure generally being adequate to engage the tube 12 with the absorbent material 35. Since the capture rate of antigenic substances by an antibody thereto is diffusion limited, it is desirable to allow the test specimen to remain in the assay tube 12 for one to ten minutes in order to ensure a threshold level of antigen capture by the antibody so that a noticeable positive result will occur in those cases where the antigen level is low, such as in the early stages of pregnancy. In other words, sufficient residency of the test specimen in the assay tube 12 is necessary to obtain the desired level of sensitivity for the assay.

A solution of an enzyme conjugated with anti-HCG is introduced into the drained assay tube 12 through the aperture 23 and again, allowed to reside in the tube 12 for one or two minutes to enable attachment of the conjugate to any HCG captured by the anti-HCG attached to the tube wall. The assay tube 12 is drained as before by contacting the lower end 17 with the absorbent material 35 and an aqueous wash solution is introduced into and drained from the tube 12 to ensure that all free enzyme conjugate is removed from the assay tube 12. Preferably, this wash step is repeated. A solution containing a substrate for the enzyme of the enzyme conjugate, plus an indicator for detecting a metabolic product of the enzyme/substrate reaction is introduced into the assay tube 12 through the aperture 23 and the positive or negative result is observed after a few minutes by the development or lack of development of the indicator colour.

Clearly, the device may be adapted for use in conducting a plurality of assays simultaneously, and as mentioned above, it is preferable to utilize an assay tube 12 in conjunction with an adjacent reference tube 13 for assisting in judging assay results.

While the foregoing description has been directed to applicant's preferred embodiment, it is felt that the principles of the invention are of broader application. Therefore, without being limited by the foregoing description, the invention is defined in the following claims.

I claim:

1. A device for performing immunoassays, comprising:
    a support structure for a transparent capillary assay tube, said tube having an internal surface to which is attached an antibody, antigen or hapten, the tube having an upper end attached to a lateral portion of the support structure so that the tube is suspended in an upright position having a lower end being free, the lateral portion defining a first aperture in flow communication with the upper end of the tube, and the support structure having an upright portion attached to the lateral portion, the upright portion being sufficiently resiliently flexible to allow downward deflection of the lateral portion, and hence, the tube upon application of moderate manual pressure; and
    absorbent material positioned beneath the capillary tube and spaced from the lower free end thereof, said lower end being engageable with the absorbent material upon downward deflection of the support structure so that liquid contained in the capillary tube may be drawn into the absorbent material.

2. A device as claimed in claim 1, further comprising a reference transparent capillary tube attached to the lateral portion adjacent said assay tube, said reference tube being free of attached antigen, antibody or hapten, and being in flow communication with a second aperture defined in the lateral portion, said reference tube having a free lower end engageable with the absorbent material upon downward deflection of the support structure.

3. A device as claimed in claim 2, wherein the first and second apertures each have an upper conically shaped portion providing a funnelled feed well for each of the assay and reference tubes.

4. A device as claimed in claim 1, wherein said first aperture has an upper conically shaped portion providing a funnelled feed well for the assay tube.

5. A device as claimed in claim 1, wherein the lateral and upright portions of the support structure are formed of a single piece of plastic.

6. A device as claimed in claim 1, further comprising a base attached to the upright portion, the upright portion extending between the lateral portion and the base.

7. A device as claimed in claim wherein the absorbent material is positioned atop the base, said material being surrounded by a containment structure which encloses the material except in the area beneath the assay tube.

8. A device for performing immunoassays, comprising:
    a support structure for a transparent capillary assay tube, said tube having an internal surface to which is attached an antibody, antigen or hapten, the tube having an upper end attached to a lateral portion of the support structure so that the tube is suspended in an upright position having a lower end being free, the lateral portion defining a first aperture in flow communication with the upper end of the tube, and the support structure having an upright portion attached to the lateral portion, the upright portion having at least one transverse groove and being sufficiently resiliently flexible to allow downward deflection of the lateral portion, and hence, the tube upon application of moderate manual pressure; and
    absorbent material positioned beneath the capillary tube and spaced from the lower free end thereof, said lower end being engageable with the absorbant material upon downward deflection of the support structure so that liquid contained in the capillary tube may be drawn into the absorbent material.

9. A device as claimed in claim 8, further comprising a reference transparent capillary tube attached to the lateral portion adjacent said assay tube, said reference tube being free of attached antigen, antibody or hapten, and being in flow communication with a second aperture defined in the lateral portion, said reference tube having a free lower end engageable with the absorbent material upon downward deflection of the support structure.

10. A device as claimed in claim 9, wherein the first and second apertures each have an upper conically shaped portion providing a funnelled feed wall for each of the assay and reference tubes.

11. A device as claimed in claim 8, wherein said first aperture has an upper conically shaped portion providing a funnelled feed well for the assay tube.

12. A device as claimed in claim 8, wherein the lateral and upright portions of the support structure are formed of a single piece of plastic.

13. A device as claimed in claim 8, further comprising a base attached to the upright portion, the upright portion extending between the lateral portion and the base.

14. A device as claimed in claim 8, wherein the absorbent material is positioned atop the base, said material being surrounded by a containment structure which encloses the material except in the area beneath the assay tube.

* * * * *